United States Patent [19]

Stemmle et al.

[11] Patent Number: 4,828,839

[45] Date of Patent: May 9, 1989

[54] METHOD FOR MAKING A GUAR FLOUR CHEWABLE DOSAGE UNIT

[75] Inventors: Berthold Stemmle, Hockenheim; Alexander Wirl, Heuchelheim; Fritz Demmer, Hirschberg-Leutershausen, all of Fed. Rep. of Germany

[73] Assignee: Boehringer Mannheim GmbH, Mannheim, Fed. Rep. of Germany

[21] Appl. No.: 149,901

[22] Filed: Jan. 29, 1988

Related U.S. Application Data

[60] Division of Ser. No. 68,725, Jun. 29, 1987, abandoned, which is a continuation of Ser. No. 442,325, Nov. 17, 1982, abandoned.

[30] Foreign Application Priority Data

Nov. 28, 1981 [DE] Fed. Rep. of Germany ....... 3147268
Mar. 11, 1982 [DE] Fed. Rep. of Germany ....... 3208768

[51] Int. Cl.$^4$ .......................... A61K 9/48; A61K 9/20
[52] U.S. Cl. ..................... 424/452; 424/439; 424/441; 424/465
[58] Field of Search ................ 424/439, 441, 465, 452

[56] References Cited

U.S. PATENT DOCUMENTS

| | | | |
|---|---|---|---|
| 2,951,791 | 9/1960 | Stearns | 424/361 |
| 3,101,299 | 8/1963 | Ferrand | 424/361 |
| 3,148,114 | 9/1964 | Fahrenbach et al. | 424/195 |
| 3,424,842 | 1/1969 | Nurnberg | 424/238 |
| 3,946,110 | 3/1976 | Hill | 424/230 |
| 4,254,099 | 3/1981 | Asmussen et al. | 424/357 |

FOREIGN PATENT DOCUMENTS

| | | |
|---|---|---|
| 0005977 | 12/1979 | European Pat. Off. . |
| 0007619 | 2/1980 | European Pat. Off. . |
| 1201014 | 8/1970 | United Kingdom . |
| 2021948 | 12/1979 | United Kingdom . |
| 2030583 | 4/1980 | United Kingdom . |

OTHER PUBLICATIONS

Brauer et al., Deutsche Apotheker 25(10):614–619 (1973).
Jenkins et al., Lancet, May 17, 1975:1116–1117.
Jenkins et al., Ann. Int. Medicine 86(1):20–23, Jan. 1977.
Abele et al., Pharmaceutica Acta Helvetiae 53(9/10):253–260, 1978.
Jenkins, David J. A. et al., "Decrease in Postprandial Insulin and Glucose Concentrations by Guar and Pectin", 1977, *Annals of Internal Medicine*, pp. 20 to 23.
Rompp, Hermann et al., *Rompps Chemie-Lexikon*, p. 1354.

*Primary Examiner*—Shep K. Rose
*Attorney, Agent, or Firm*—Felfe & Lynch

[57] ABSTRACT

The present invention provides a composition containing guar flour in the form of tablets for oral administration, said tablets having been produced by dry pressing guar flour with a particle size of 60 to 500 μm. in admixture with 5 to 30% of highly dispersed silica gel.

7 Claims, No Drawings

METHOD FOR MAKING A GUAR FLOUR CHEWABLE DOSAGE UNIT

This application is a division of application Ser. No. 068,725, filed June 29, 1987 which is a continuation of Ser. No. 442,325, filed Nov. 17, 1982, both now abandoned.

The present invention is concerned with compositions containing guar flour for oral administration and with a process for the production thereof.

Guar flour (guar gum) is a natural hydrocolloid which is present in the endosperm of the guar plant (*Cyamopsis tetragonoloba*) and is a polysaccharide comprising galactose and mannose units. The quality and fineness of the guar flour obtained by grinding the endosperm after removal of the husk and cotyledon are determined by the physical and mechanical pre- and post-treatment. Guar flour is usually employed as a thickening agent for dressings and finishes, as an emulsifier for paper pasting, as an additive for flotation agents and, to a certain extent, as a thickening and gelling agent, for example in the manufacture of icecream (see Rompps, *Chemie-Lexikon*, 7th edition, page 1354).

It is known, for example (see Jenkins et al., *The Lancet*, 1975, 1116; 1977, 779) that guar flour, when administered to patients in comparatively large amounts, significantly lowers the blood cholesterol and glucose level. Guar flour can, therefore, be used in the treatment of hyperglycaemia and hyper lipoproteinaemia. However, the administration of the necessary, comparatively-large amounts of guar flour (10 to 30 g. per day in 3 to 5 doses) represents a considerable problem because guar flour is very hydrophilic and, in admixture with water, rapidly forms gels. In the case of a direct administration in the form of a dry powder, the guar flour would, therefore, adhere to the oral and pharyngeal cavity in an unpleasant way and, due to subsequent swelling in the oesophagus, can even result in blockages and serious disturbances of the wellbeing of the patient. A mixture with comparatively small quantities of water results in the formation of sticky lumps which, because of the high viscosity of the surface layer, only dissolve very slowly. A homogeneous mixture is only obtained when the guar flour is introduced, with vigorous stirring, into an at least hundredfold amount of water. Because of its high viscosity, this gel is difficult to swallow and many patients find it to be unpleasant.

British Patent Specifications Nos. 2,021,948 and 2,030,583 describe guar granulates in which, by coating the guar particles with starch or proteins or by special selection of the guar flour used (particle size 100 to 1000 μm) and granulation of these substances with an insufficient amount of water, a granulate is produced which can only be suspended in a comparatively large amount of water but which only swells up to a highly viscous gel after some minutes so that this mixture can be imbibed. A similar preparation is known from European Patent Specification No. 007619 in which the guar particles are enveloped by a layer of gelatine and possibly additionally impregnated with an alkaline buffer. This preparation can also be suspended in water and can be administered in this manner since the particles only swell to form a viscous gel after a few minutes or in the acidic medium of the stomach. However, products of this type are not suitable for dry administration or for administration with only a small amount of liquid since the swelling of such granulates takes place partly in the mouth in spite of the retarding.

From European Patent Specification No. 005977, it is also known to bake guar flour, with appropriate additives, to make bread or biscuits. Quite apart from the fact that the baking damages the guar flour and makes it partly ineffective, such a "bread" usually only contains 5 to 20% of guar so that, for dietetic purposes, undesirably large amounts of the mixture (about 200 g.) must be administered daily.

Therefore, for use as a medicament, there is the problem of bringing guar flour into a form which can be administered orally and which can be ingested by patients without difficulty and in comparatively large amounts. Because of the viscosity of the solutions, for this purpose only a dry form comes into consideration which, on the one hand, does not result in adhesion in the oral and pharyngeal cavity but, on the other hand, is rapidly dissolved and swollen in the stomach so that the agent becomes fully effective without forming dry lumps covered with a viscous slime. Furthermore, the smallest possible proportion of adjuvant materials is also desirable in order not to unnecessarily increase the amounts of substance which are, in any case, quite large. The choice of adjuvant materials is also limited by the fact that the product must be administered frequently for quite long periods of time and, therefore, should possess a neutral or pleasant taste. In addition, the product should be capable of administration either in a dry form or with only a small amount of liquid and should also contain little or no powdered components which would tend to adhere to the mouth.

It has been found that a moist granulation preceding the tabletting, such as is deemed to be necessary according to the above-mentioned literature, results in such a marked reduction of the ability to swell that corresponding tablets only break down into comparatively large granulate particles which are enveloped by a viscous slimy layer of guar and which substantially do not dissolve in the course of passing through the gastrointestinal tract. Working up with additional adjuvants which are known either to increase the breakdown of tablets or to increase the swellability of tablets, such as cross-linked polyvinylpyrrolidone, sodium carboxymethyl starch, maize starch, microcrystalline cellulose and the like, also do not give satisfactory products, after previous granulation or in the case of direct pressing to give tablets, because, in the case of a comparatively high pressure, tablets are obtained which are not sufficiently swellable or, in the case of low pressure, the tablets obtained have a sufficient swellability but have such a low degree of hardness that, upon further handling, they break or have too great an amount of powdery fines. In the case of adding starch in an amount of up to 20%, tablets cannot be produced at all since a pressing force of up to 7000N, is required and the formed bodies again break down to powder.

Surprisingly, we have now found that sufficiently hard and non-breakable guar tablets can be produced when dry guar flour is mixed with 5 to 30% by weight and preferably with 10 to 15% by weight of highly dispersed silica gel and then sufficiently dry pressed to form tablets.

In addition, we have, surprisingly, also ascertained that very fine guar flour which, as is known, dissolves especially well and rapidly in water, is less suitable for the purposes of the present invention that coarser material which dissolves much more slowly since fine particles (smaller than 60 μm) apparently flow together at comparatively high pressures and more or less envelop the added silica gel so that the breakdown of the tablets into individual particles and thus the swellability rapidly decreases when using high pressures. On the other hand, particles with a size of more than 60 μm and preferably with a size of from about 60 to 500 μm do not flow together even at high pressures so that tablets produced in this manner have a swellability which is relatively independent of the pressure employed. Therefore, from such a guar flour, it is possible to produce hard and wear-resistant tablets which are especially suitable for oral administration and which, nevertheless, possess a sufficiently high swellability.

As is to be expected, the swellability of the tablets produced is the greater, the higher is the proportion of added silica gel and the lower is the pressure employed, i.e. the lower is the hardness of the tablets produced. On the other hand, of course, with decreasing hardness, the powdery fines also increase when handling such tablets.

In order to improve the tabletting, if desired, there can be added to the formulation up to 5% and preferably 1 to 5% of a conventional binding agent, such as a polyethylene glycol, starch or polyvinylpyrrolidone.

Since the form of composition according to the present invention is to be swallowed dry or with only a small amount of liquid for after-rinsing, it has proved to be advantageous to administer a number of comparatively small tablets instead of one large tablet. For production-technical reasons, tablets with a diameter of from 3 to 5 mm. and a height of 1 to 3 mm. are preferred, these tablets preferably having a hardness of more than 30N. Because of the small proportion of adjuvant in these preparations, 100 to 200 of such tablets suffice for each dosing. Administration can be further facilitated by means of a thin dragee covering of sugar or of a film-forming, water-soluble polymer.

In the case of attempts further to improve the acceptance of such tablets by adding thereto aroma substances, acids and sweetening agents, in order to produce not only a neutral but also a pleasant taste insofar as the patients chew the tablets, unexpected difficulties arose. It was found that when storing such products, after only 6 months at 35° C., a structural breakdown of the guar flour took place which resulted in a reduction of the swellability and of the rate of swelling. Due to the presence of the aroma substances, it was not possible to ascertain whether an impairment of the flavour also took place simultaneously.

Since swellability and rate of swelling are important qualtity criteria of the pharmacological effectiveness, it was necessary to find a means of imparting an aroma which did not change these properties of the base guar material. Neither a change of the added acid (experiments were made with all conventional foodstuff acids, such as citric acid, malic acid, tartaric acid, ascorbic acid, gluconic acid, fumaric acid and succinic acid), nor a change of the aroma substance (such as lemon essence, raspberry, strawberry, bilberry, apricot and cherry aroma, in which cases there can be used not only synthetic but also natural aroma substances), changed in any way the undesirable breakdown of the guar flour.

Therefore, there was the problem of finding other additives which, on the one hand, did not change the pleasant taste of the aroma-containing tablets and, on the other hand, prevented the breakdown of the guar flour or at least slowed it down to such an extent that it no longer had a disturbing effect. Surprisingly, we have found that this stabilisation can be sucessfully accomplished when the acids which bring about the fresh flavour of such aroma-containing tablets and which are present in an amount of from 1 to 10% are, before the admixture thereof, coated with an amount of from 1 to 20% and preferably of about 2 to 10%, referred to the acid, of a hydrophobing agent. Referred to the mixture as a whole, the coating only constitutes an amount of from 0.01 to 2%. As hydrophobing agents, they are preferably used saturated and unsaturated solid fatty acids, mono-, di- and triglycerides thereof, natural and synthetic waxes, wax alcohols or mixtures thereof, but other hydrophobic adjuvants such as talc, magnesium stearate, polymers, such as of methacrylic acid or of methacrylic acid esters can be used alone or as mixtures.

The acids used can be any of the known foodstuff acids, those mentioned above being preferred because of their ready availability.

The above-mentioned aroma materials can be present in an amount of from 0.5 to 3% and preferably of from about 0.8 to 2%.

It must be regarded as being surprising that, on the one hand, the addition of relatively small amounts of a solid acid in powder form to the tablet formulation brings about a change of the guar flour at all and, on the other hand, that by the addition of a substantially even smaller amount of a hydrophobing agent, this negative effect can again be removed.

Since guar flour must be administered in very large dosages (10 to 30 g. per day) in order to initiate a pharmacological effect, guar formulations must, on the other hand, contain an unusually high proportion of guar and the smallest possible proportion of adjuvants. Under these circumstances, it is extremely advantageous that it is possible, in the above-described manner, to produce, with only small additional amounts of adjuvant, stable formulations in which the proportion of guar in the formulation as a whole amounts to from 50 to more than 90%.

The present invention also provides a process for the production of the new compositions, wherein the components are dry mixed and compressed in a tabletting press at a pressure of from 3000 to 15000N/cm$^2$, and encapsulating the composition in the tablet form of a plurality of tablets into a dosage unit.

In the following Table, there are compared the relative dynamic viscosities of various tablet batches produced according to the present invention and without the additive used according to the present invention but which otherwise have an identical composition and are prepared in the same manner.

The determination of the relative dynamic viscosity in dependence upon time is carried out with a rotation viscosimeter (Contraves AG, Zürich, Switzerland, Epprecht Rheomat 15 Type). The swelling of the miniature tablets (corresponding to 10 g. of guar gum) takes place in a round-bottomed flask containing 800 ml. of water at 37° C. while stirring with a paddle stirrer (90 r.p.m.). At definite intervals of time, samples are taken which are introduced into the measurement beaker of the above-mentioned rotation viscosimeter and the viscosity determined at a spindle rate adjustment of 10 scale units. The measurement system of the rotation viscosimeter is also thermostated at 37° C., using measurement system C.

| composition | (%) | batch | relative dynamic viscosity with thermal stressing 6 weeks | | | after 2 hrs. (PA.s) 6 months | |
|---|---|---|---|---|---|---|---|
| | | | KS$^{(2)}$ | ·35° C. | 45° C. | KS$^{(2)}$ | 35° C. |
| guar gum | 81.5 | 1 | 1.3 | 0.6 | 0.5 | | |
| free citric acid | 3.7 | 2 | 1.2 | 1.1 | 0.8 | 0.8 | 0.3 |
| inert adjuvants | 14.8 | | | | | | |
| guar gum | 81.5 | 3 | 1.4 | 1.2 | 1.2 | | |
| hydrophobed citric acid | 3.7 | 4 | 1.3 | 1.2 | 1.3 | | |
| inert adjuvants | 14.8 | 5 | 1.4 | 1.3 | 1.2 | 1.3 | 1.4 |

The following Examples illustrate the influence of the tabletting pressure, the composition of the adjuvants and the particle size of the guar on the hardness of the tablets and the swellability thereof.

EXAMPLE 1

Swellability and physical parameters of a formulation according to the present invention containing 10% of highly dispersed silica gel and 2% of binding agent (Formulation I) in comparison with analogous formulations with microcrystalline cellulose (Formulation II), cross-linked polyvinylpyrrolidone (Formulation III), sodium carboxymethylstarch (Formulation IV) and maize starch (Formulation V).

| Formulation No. | pressing force (N) | hardness$^{(1)}$ (N) | wear$^{(2)}$ (%) | viscosity $\eta_{rel}$ in Pa.s$^{(3)}$ | |
|---|---|---|---|---|---|
| | | | | 0.5 hrs. | 1.0 hrs. |
| I | 2000 | 44.1 | 3.4 | 1.046 | 1.199 |
| II | 1450 | 33.8 | 11.93 | 0.270 | 0.270 |
| III | 3000 | 10 | 17.2 | 1.055 | 1.226 |
| IV | 7000 | — | — | — | — |
| V | 7000 | — | — | — | — |

Compositions of Formulations I to V and production process

| component | Composition (%) of formulation | | | | |
|---|---|---|---|---|---|
| | I | II | III | IV | V |
| guar gum | 88.24 | 88.24 | 88.24 | 88.24 | 88.24 |
| Macrogol 6000 | 1.96 | 1.96 | 1.96 | 1.96 | 1.96 |
| highly dispersed silica gel | 9.80 | — | — | — | — |
| microcrystalline cellulose | — | 9.80 | — | — | — |
| cross-linked polyvinyl-pyrrolidone | — | — | 9.80 | — | — |
| sodium carboxymethyl starch | — | — | — | 9.80 | — |
| maize starch | — | — | — | — | 9.80 |

All the components were mixed and pressed to give miniature tablets (diameter 5 mm., height 2 mm.).

EXAMPLE 2

Swellability of guar miniature tablets of Formulation I according to the present invention with "fine" and "coarse" guar gum, as well as physical parameters:

| Formulation | hardness (N)$^{(1)}$ | wear (%) | pressing force (N) | viscosity $\eta_{rel}$ in Pa.s$^{(3)}$ | |
|---|---|---|---|---|---|
| | | | | 0.5 hrs. | 1.0 hrs. |
| with "fine" guar gum, less than 60 μm. | 16 | 23 | 900 | 1.307 | 1.496 |
| | 76 | 1.2 | 2400 | — | 0.270 |
| with "coarse" guar gum, more than 60 μm. | 16 | 65 | 1200 | 0.883 | 1.118 |
| | 64 | 2.2 | 2600 | 0.847 | 1.118 |

$^{(1)}$Schleuninger tester, amount: 5 miniature tablets
$^{(2)}$Roche friabilator
$^{(3)}$The determination of the relative dynamic viscosity in dependence upon time is carried out with a rotation viscosimeter (Contraves A. G. Zurich, Switzerland, Epprecht Rheomat 15 Type) in the above-described manner.

It will be understood that the specification and examples are illustrative but not limitative of the present invention and that other embodiments within the spirit and scope of the invention will suggest themselves to those skilled in the art.

What is claimed is:

1. A process for making a guar flour chewable dosage unit comprising:
   (a) providing a guar flour having a particle size of from about 60 μm to about 500 μm;
   (b) admixing highly dispersed silica gel with the guar flour from about 5% to about 30% by weight;
   (c) compressing the admixture in a tabletting press with a pressure of from about 3000N/cm$^2$ to form tablets of the admixture of guar flour and silica gel, and;
   (d) encapsulating a plurality of 100 to 200 of the compressed miniature tablets into a chewable dosage unit to be swallowed dry, or with only small amounts of liquid.

2. A process according to claim 1, and additionally comprising adding to the admixture up to about 5% by weight of a conventional binding agent.

3. A process according to claim 1, wherein the pressing produces tablets having a diameter of about 2 mm. to about 5 mm., a thickness of about 1 mm. to about 4 mm., and a hardness of more than 30N.

4. A process according to claim 1, and additionally comprising adding to the admixture about 0.5% to about 3% of aroma material and about 1% to about 10% of a carboxylic acid suitable for human consumption, the acid being coated with about 1% to about 20% of its weight with a hydrophobing agent.

5. A process according to claim 4, and additionally comprising selecting the hydrophobing agent from one or more of the group consisting of a saturated or unsaturated solid fatty acid, a mono- di- or triglyceride thereof, a natural or synthetic wax, a wax alcohol, talc, magnesium stearate and a polymer.

6. A process according to claim 5, and additionally comprising selecting the carboxylic acid from the group consisting of citric acid, malic acid, tartaric acid, ascorbic acid, gluconic acid, fumaric acid, and succinic acid.

7. The process of claim 5, wherein said polymer is methacrylic acid or a methacrylic acid ester.

* * * * *